(12) United States Patent
Nova

(10) Patent No.: US 9,907,971 B2
(45) Date of Patent: *Mar. 6, 2018

(54) MEDICAL DEVICE ADJUSTING OPERATION WHEN USED WITH NON-AUTHENTICATED PATIENT PARAMETER COLLECTING ACCESSORY

(71) Applicant: Physio-Control, Inc., Redmond, WA (US)

(72) Inventor: Richard C. Nova, Kirkland, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/156,258

(22) Filed: May 16, 2016

(65) Prior Publication Data

US 2016/0256698 A1    Sep. 8, 2016

Related U.S. Application Data

(63) Continuation of application No. 14/678,742, filed on Apr. 3, 2015, now Pat. No. 9,339,661, which is a (Continued)

(51) Int. Cl.
*A61N 1/39* (2006.01)
*A61B 5/01* (2006.01)
(Continued)

(52) U.S. Cl.
CPC .............. *A61N 1/3931* (2013.01); *A61B 5/01* (2013.01); *A61B 5/021* (2013.01); *A61B 5/0215* (2013.01);
(Continued)

(58) Field of Classification Search
CPC .......................... A61N 1/3931; A61N 1/3993
See application file for complete search history.

(56) References Cited

U.S. PATENT DOCUMENTS 5,321,392 A    6/1994  Skakoon et al.
5,702,431 A   12/1997  Wang et al.
(Continued)

FOREIGN PATENT DOCUMENTS

KR    1020040095307 A    11/2004

OTHER PUBLICATIONS

International Preliminary Report on Patentability for PCT/US2009/045943, dated Sep. 1, 2010, 12 pages.
(Continued)

*Primary Examiner* — Joseph Dietrich
(74) *Attorney, Agent, or Firm* — Lane Powell, PC

(57) ABSTRACT

Embodiments are directed to a medical device, such as a defibrillator, for use with an accessory capable of collecting a parameter of a patient. The medical device is capable of at least performing a basic functionality, an advanced functionality, and of defibrillating the patient. The medical device includes an energy storage module within a housing for storing an electrical charge that is to be delivered to the patient for the defibrillating. The medical device includes a processor structured to determine whether a data set received from the accessory confirms or not a preset authentication criterion about the accessory. Although when the accessory is coupled to the housing the medical device is capable of the defibrillating and the basic functionality, the medical device is capable of the advanced functionality only when the accessory is coupled to the housing and it is determined that the preset authentication criterion is confirmed. Embodiments also include methods of operation and a programmed solution.

20 Claims, 7 Drawing Sheets

MEDICAL DEVICE AND ATTACHED
AUTHORIZED ACCESSORY

Related U.S. Application Data continuation of application No. 13/445,776, filed on Apr. 12, 2012, now Pat. No. 9,008,766, which is a continuation-in-part of application No. 12/760,331, filed on Apr. 14, 2010, now Pat. No. 8,183,823, and a continuation-in-part of application No. 12/760,378, filed on Apr. 14, 2010, now Pat. No. 8,179,087, said application No. 12/760,331 is a continuation-in-part of application No. 12/131,267, filed on Jun. 2, 2008, now Pat. No. 7,728,548, said application No. 12/760,378 is a continuation-in-part of application No. 12/131,267, filed on Jun. 2, 2008, now Pat. No. 7,728,548.

(51) Int. Cl.
| | |
|---|---|
| A61B 5/021 | (2006.01) |
| A61B 5/0215 | (2006.01) |
| A61B 5/0408 | (2006.01) |
| A61B 5/08 | (2006.01) |
| A61B 5/1455 | (2006.01) |
| G06F 17/30 | (2006.01) |
| G06F 21/60 | (2013.01) |
| H01M 2/34 | (2006.01) |
| H01M 6/50 | (2006.01) |
| H01M 10/42 | (2006.01) |
| H01M 16/00 | (2006.01) |
| H02J 7/00 | (2006.01) |
| H02J 7/34 | (2006.01) |

(52) U.S. Cl.
CPC ........ *A61B 5/0408* (2013.01); *A61B 5/04085* (2013.01); *A61B 5/082* (2013.01); *A61B 5/14552* (2013.01); *A61N 1/3975* (2013.01); *G06F 17/30424* (2013.01); *G06F 21/602* (2013.01); *H01M 10/425* (2013.01); *A61B 2560/0214* (2013.01); *H01M 2/34* (2013.01); *H01M 6/5033* (2013.01); *H01M 10/4221* (2013.01); *H01M 16/00* (2013.01); *H02J 7/0063* (2013.01); *H02J 7/345* (2013.01)

(56) References Cited

U.S. PATENT DOCUMENTS

| | | |
|---|---|---|
| 5,721,482 A | 2/1998 | Benvegar et al. |
| 5,939,856 A | 8/1999 | Demuro et al. |
| 6,072,229 A | 6/2000 | Steijer et al. |
| 6,072,299 A | 6/2000 | Kurle et al. |
| 6,127,063 A | 10/2000 | Kowalsky et al. |
| 6,181,102 B1 | 1/2001 | Andrews et al. |
| 6,223,077 B1 | 4/2001 | Schweizer et al. |
| 6,249,105 B1 | 6/2001 | Andrews et al. |
| 6,291,966 B1 | 9/2001 | Wendelrup et al. |
| 6,438,415 B1 | 8/2002 | Powers |
| 6,639,381 B2 | 10/2003 | Tamura et al. |
| 6,873,133 B1 | 3/2005 | Kavounas |
| 6,972,542 B2 | 12/2005 | Patino et al. |
| 7,095,210 B2 | 8/2006 | Tamura et al. |
| 7,250,612 B2 | 7/2007 | Pai-Paranjape et al. |
| 7,728,548 B2 | 6/2010 | Daynes et al. |
| 8,229,562 B2 | 7/2012 | Ginggen et al. |
| 2003/0195581 A1 | 10/2003 | Meadows et al. |
| 2004/0039257 A1 | 2/2004 | Hickle |
| 2006/0178170 A1 | 8/2006 | Chung et al. |
| 2007/0143864 A1 | 6/2007 | Cabana et al. |
| 2008/0077185 A1 | 3/2008 | Pearce et al. |
| 2008/0140163 A1 | 6/2008 | Keacher et al. |
| 2010/0198286 A1 | 8/2010 | Neumiller et al. |
| 2010/0198287 A1 | 8/2010 | Neumiller et al. |

OTHER PUBLICATIONS

Response to Written Opinion for International Application No. PCT/US209/045943, filed Aug. 2, 2010, 18 pp.

International Search Report and Written Opinion of International Application No. PCT/US2009/045943, dated May 4, 2010, 14 pages.

U.S. Appl. No. 12/760,378, by James S. Neumiller, filed Apr. 14, 2010.

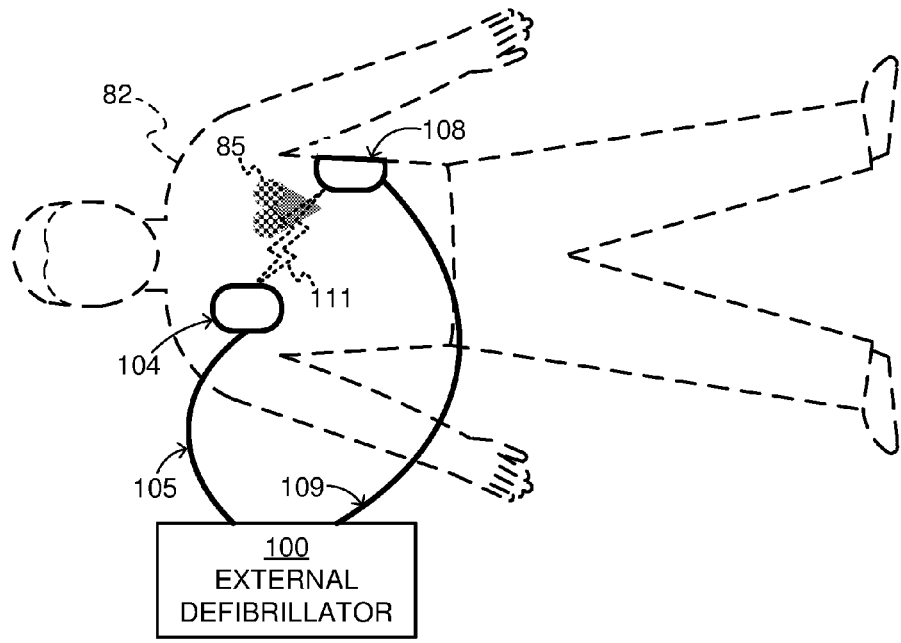
FIG. 1 *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2 *TWO MAIN TYPES OF EXTERNAL DEFIBRILLATORS*

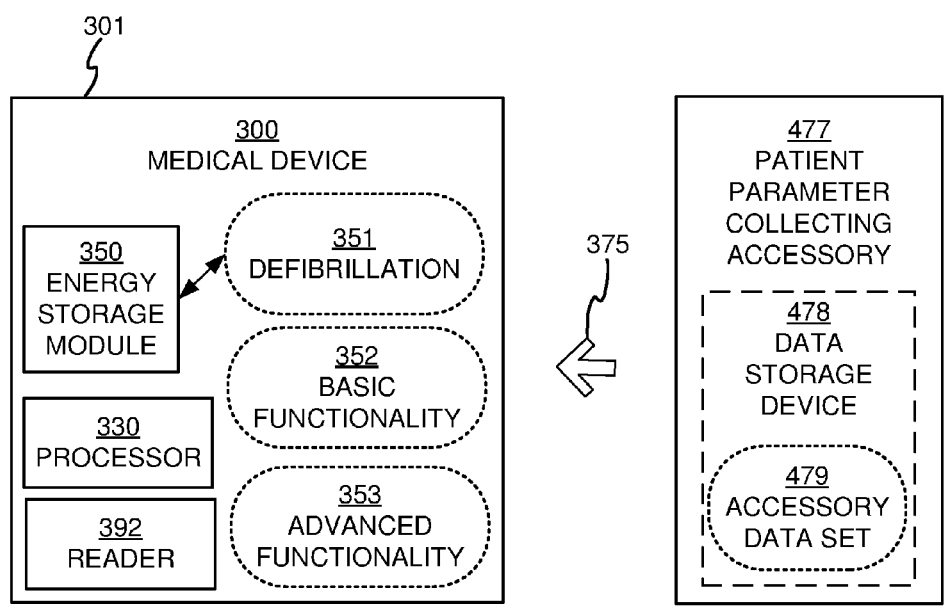
FIG. 3   MEDICAL DEVICE WITH READER/ VALIDATOR FOR ACCESSORY

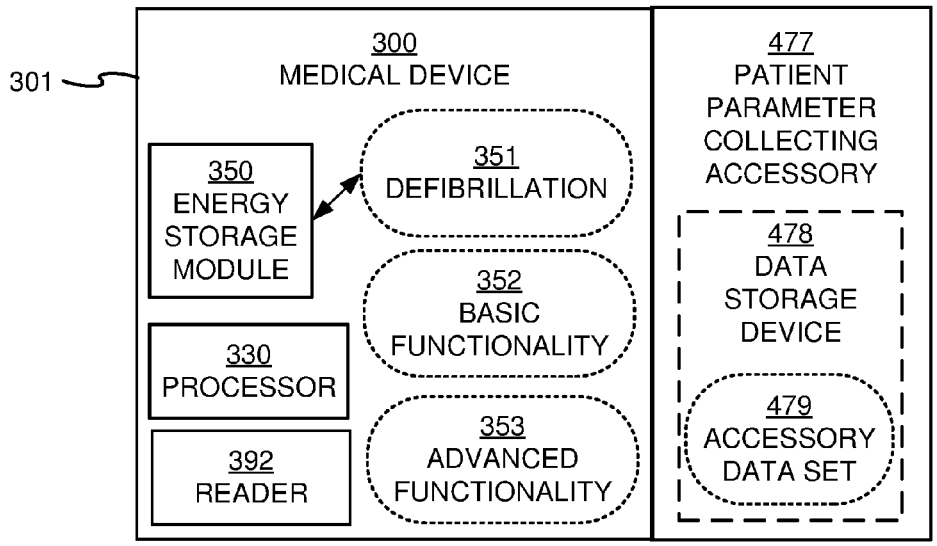
FIG. 4 *MEDICAL DEVICE AND ATTACHED AUTHORIZED ACCESSORY*
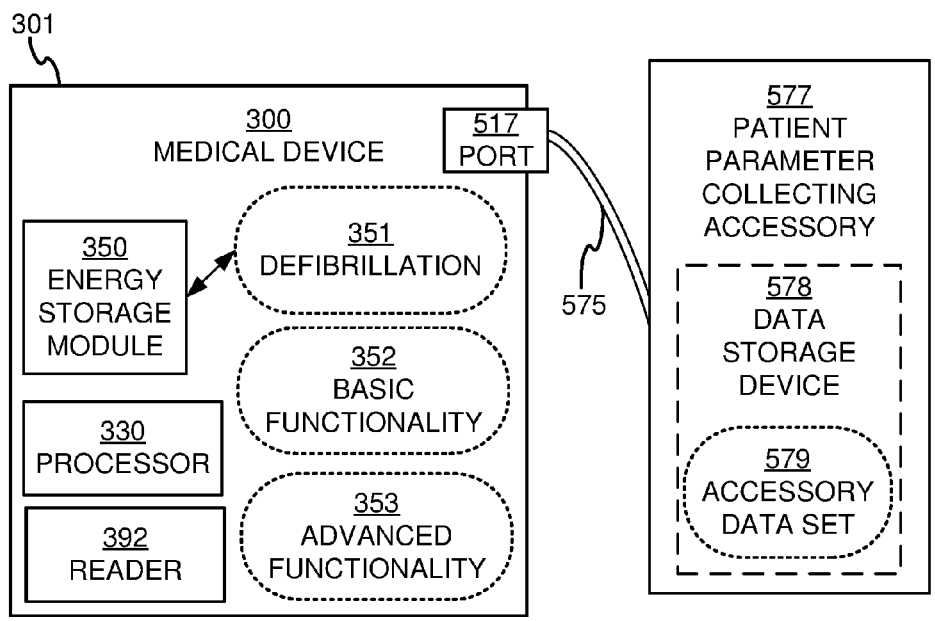
FIG. 5 *MEDICAL DEVICE AND ATTACHED AUTHORIZED ACCESSORY*

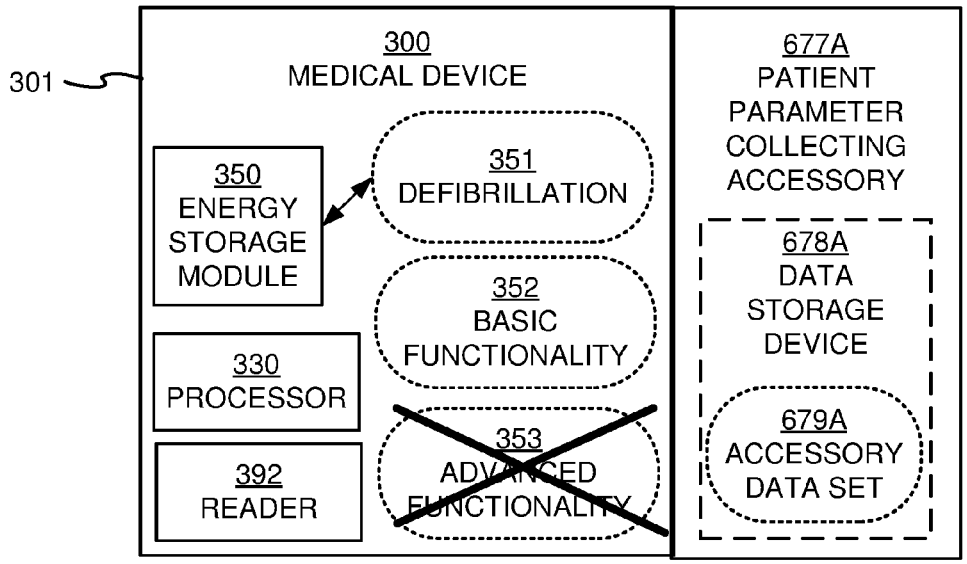
FIG. 6A *MEDICAL DEVICE AND ATTACHED UNAUTHORIZED ACCESSORY*
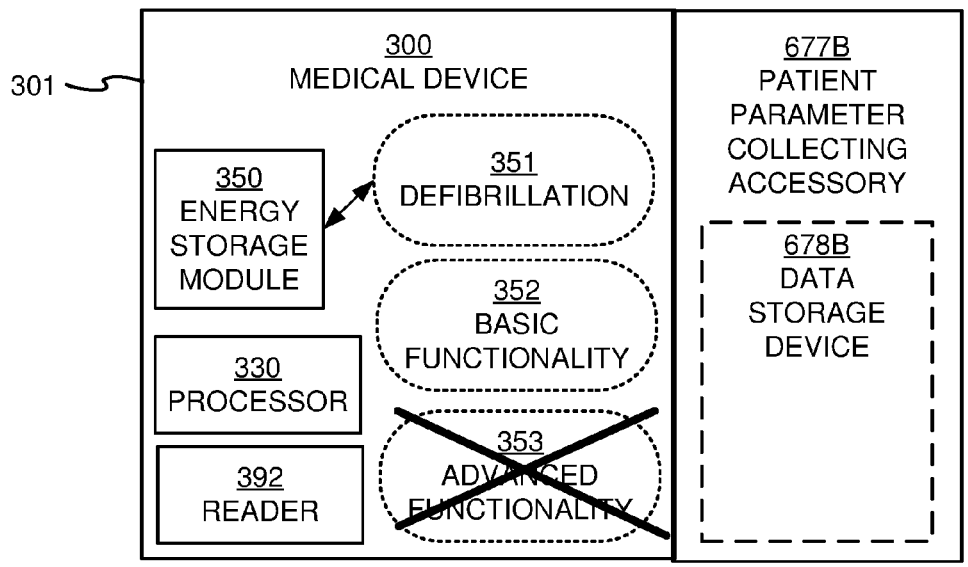
FIG. 6B *MEDICAL DEVICE AND ATTACHED UNAUTHORIZED ACCESSORY*

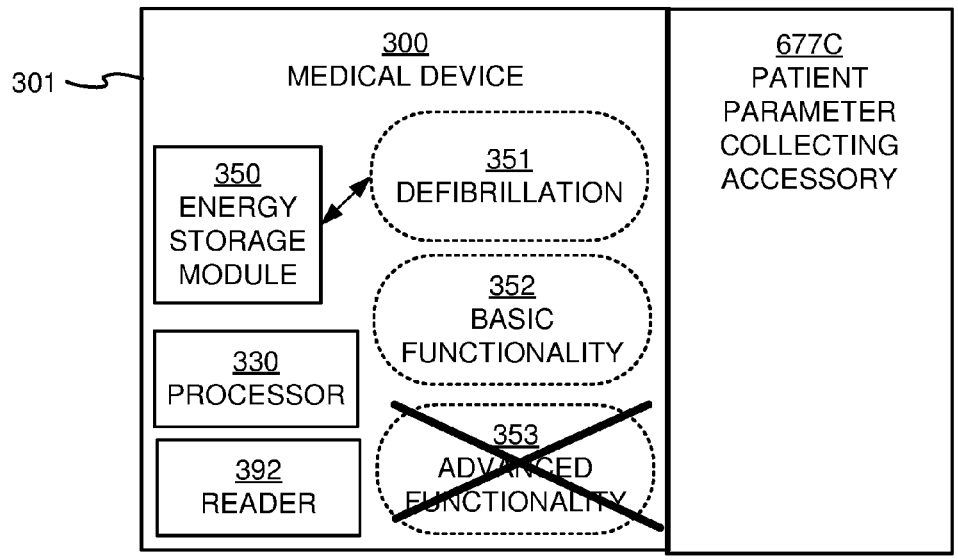
FIG. 6C *MEDICAL DEVICE AND ATTACHED UNAUTHORIZED ACCESSORY*
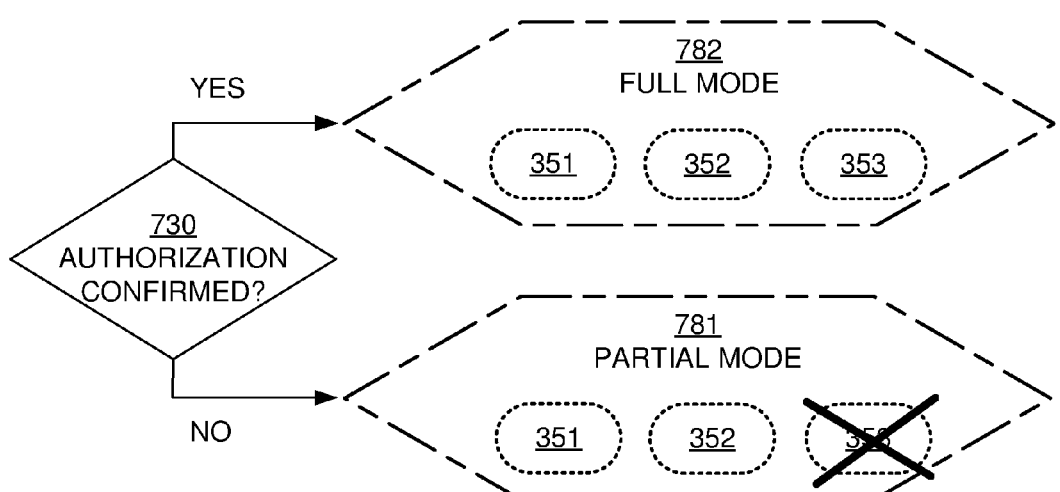
FIG. 7 *OPERATION OF MEDICAL DEVICE*

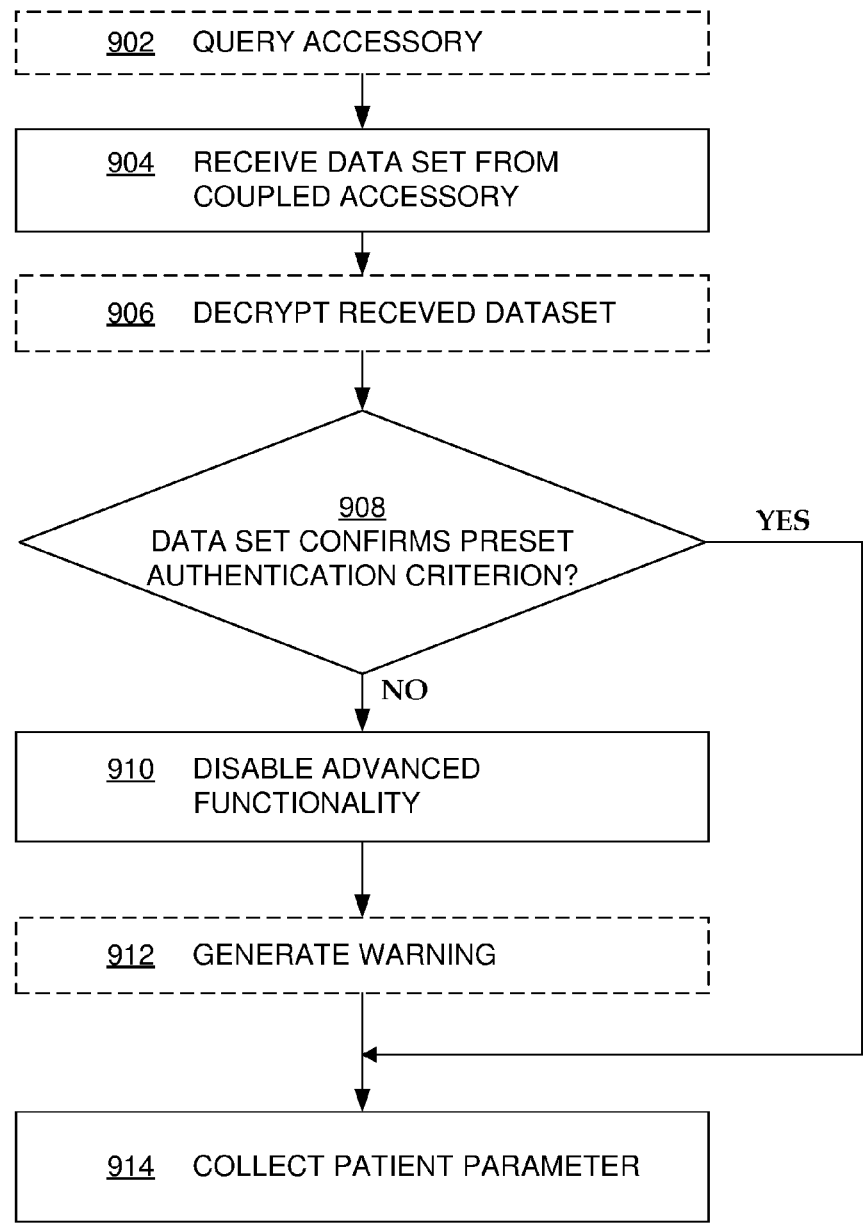
FIG. 9     *METHODS*

MEDICAL DEVICE ADJUSTING OPERATION WHEN USED WITH NON-AUTHENTICATED PATIENT PARAMETER COLLECTING ACCESSORY

CROSS REFERENCE TO RELATED PATENT APPLICATIONS

This patent application is a continuation of U.S. patent application Ser. No. 14/678,742, filed Apr. 3, 2015, entitled MEDICAL DEVICE ADJUSTING OPERATION WHEN USED WITH NON-AUTHENTICATED PATIENT PARAMETER COLLECTING ACCESSORY, currently pending, which is a continuation of U.S. patent application Ser. No. 13/445,776, filed Apr. 12, 2012, entitled MEDICAL DEVICE ADJUSTING OPERATION WHEN USED WITH NON-AUTHENTICATED PATIENT PARAMETER COLLECTING ACCESSORY, issued as U.S. Pat. No. 9,008,766, which is a continuation-in-part of U.S. patent application Ser. No. 12/760,331, filed Apr. 14, 2010, entitled SELECTIVE POWERING OF MEDICAL DEVICE DEPENDING ON AUTHENTICATION OF POWER ADAPTER SYSTEM, issued as U.S. Pat. No. 8,183,823. The U.S. Ser. No. 13/445,776 application is a continuation-in-part application of U.S. patent application Ser. No. 12/760,378, filed Apr. 14, 2010, entitled SELECTIVE RECHARGING OF MEDICAL DEVICE DEPENDING ON AUTHENTICATION OF POWER ADAPTER SYSTEM, issued as U.S. Pat. No. 8,179,087.

Both U.S. patent application Ser. Nos. 12/760,331 and 12/760,378 are continuations-in-part of U.S. patent application Ser. No. 12/131,267, entitled DEFIBRILLATOR BATTERY AUTHENTICATION SYSTEM filed on Jun. 2, 2008, which is now U.S. Pat. No. 7,728,548. All of the above-referenced patents and patent applications are incorporated by reference herein.

FIELD

This invention generally relates to medical devices and accessories for them.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body. The heart chambers pump because of the heart's electrical control system. More particularly, the sinoatrial (SA) node generates an electrical impulse, which generates further electrical signals. These further signals cause the above-described contractions of the various chambers in the heart, in the right sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia, and some of it may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Proper treatment and cure of patients oftentimes includes using medical devices. Many of these medical devices, such as defibrillators, use accessories. These accessories are typically replaced more often than the device itself, for example due to wear. Other accessories are intended to be used for only one patient, and are therefore replaced each time the medical device is used with a new patient.

Accessories are typically produced by either the device manufacturer or a party authorized by the device manufacturer. These accessories are made to exacting standards to work properly with the device. Some companies may make accessories that are not authorized by the device manufacturer but still may work with the device. These accessories are known as unauthorized accessories. Sometimes unauthorized accessories are made to lower quality standards than authorized accessories. Due to this lower quality, some unauthorized accessories can cause the device to not function as well, or even cause it to malfunction, both of which may compromise patient care. Oftentimes, users may not be able to distinguish between authorized and un-authorized accessories because some unauthorized accessories are produced and marked to appear as authorized accessories. Thus, there is no way to tell from looking at an accessory whether it will operate properly, in the case of an authorized accessory, or may comprise patient care, in the case of an unauthorized accessory.

Embodiments of the invention address these and other limitations of the prior art.

BRIEF SUMMARY

The present description gives instances of devices, systems, software and methods, the use of which may help overcome problems and limitations of the prior art.

Embodiments include a medical device for use with an accessory capable of collecting a parameter of a patient, the medical device capable of at least a basic functionality, an advanced functionality, and of defibrillating the patient. The device includes a housing structured to couple with the accessory and an energy storage module within the housing for storing an electrical charge that is to be delivered to the patient for the defibrillating. The device also includes a processor in the housing structured to determine whether a data set received from the accessory confirms or not a preset authentication criterion about the accessory. When the accessory is coupled to the housing, the medical device is capable of the defibrillating and the basic functionality. The medical device is additionally capable of the advanced functionality only when the accessory is coupled to the housing and it is determined that the preset authentication criterion is confirmed.

Other embodiments include a method in a medical device for use with an accessory capable of collecting a parameter of a patient and capable of at least a basic functionality, an advanced functionality, and of defibrillating the patient. The method includes enabling the defibrillating ability of the medical device, enabling the basic functionality of the medical device, and enabling the advanced functionality of the medical device. After the accessory is coupled to the medical device, the method determines whether a data set received from the accessory confirms or not a preset authentication criterion about the coupled accessory. The method also disables the advanced functionality of the medical device after it is determined that the preset authentication criterion is not confirmed about the coupled accessory.

An advantage over the prior art is that users of such devices can be secure knowing that patient care is not being compromised by using unauthorized, and perhaps inferior, accessories.

In some embodiments, critical functionality of the medical device is not put at risk due to operation with a faulty, unauthorized accessory. In some embodiments, operators of a medical device are informed early when unauthorized accessories are coupled to the device, alerting such operators of the possibility of compromised patient care. In some embodiments, when the advanced functionality is blocked, operators are informed before such functionality is medically necessary.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 3 is a block diagram of an external defibrillator medical device made according to embodiments, before an accessory has been attached.

FIG. 4 is a block diagram of the medical device of FIG. 3, after an authorized accessory has been attached.

FIG. 5 is a block diagram of the medical device of FIG. 3, after another authorized accessory has been attached, using a different attachment method than in FIG. 4.

FIG. 6A is a block diagram of the medical device of FIG. 3, after an example unauthorized accessory has been attached.

FIG. 6B is a block diagram of the medical device of FIG. 3, after another example unauthorized accessory has been attached.

FIG. 6C is a block diagram of the medical device of FIG. 3, after one more example unauthorized accessory has been attached.

FIG. 7 is a conceptual diagram for explaining an operation of the medical device of FIG. 3.

FIG. 9 is a detailed flow diagram illustrating example methods according to embodiments of the invention.

DETAILED DESCRIPTION

Figure 8:
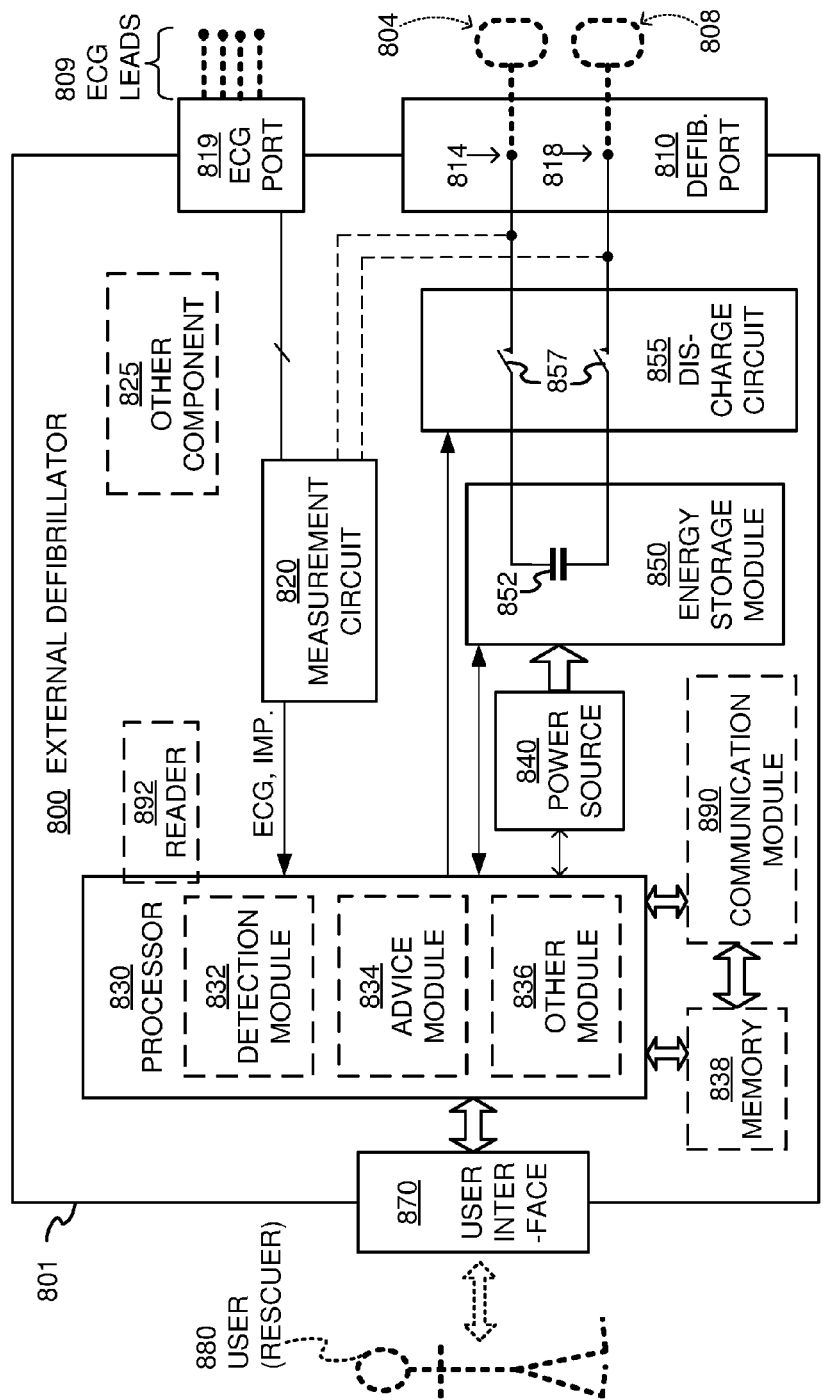
FIG. 8 is a detailed block diagram of an example external defibrillator, such as that shown in FIG. 3, showing additional components that may be included according to embodiments.

As has been mentioned, the present description is about medical devices, methods of operating such medical devices, and a programmed processor to control such medical devices for controlling enabling features of the medical device based on a determination of whether an authorized accessory is attached.

Embodiments are now described in more detail.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a block diagram of an external defibrillator medical device made according to embodiments, before an accessory has been attached. A medical device 300 may use an accessory 477 capable of collecting a parameter of a patient, such as the patient 82 of FIG. 1. The medical device 300 is capable of at least a basic functionality 352, an advanced functionality 353, and of defibrillating the patient 351. The medical device 300 includes a housing 301 structured to couple with the accessory 477. The medical device 300 also includes an energy storage module 350 within the housing 301 for storing an electrical charge that is to be delivered to the patient for the defibrillating of the patient. Also within the housing 301 of the medical device 300 is a processor 330 structured to determine whether a data set 479 received from the accessory 477 confirms or not a preset authentication criterion about the accessory. This authentication criterion is used by the medical device 300 to determine if the accessory 477 is an authorized accessory, and, based on the determination of whether an authorized accessory is attached or coupled to the medical device, set a level of services or cause other actions to occur.

The accessory 477 includes a data storage device 478, which stores an accessory data set 479. The data set 479 may be read by the medical device 300, as described below, and a determination made from the data set used to set a level of functionality for the medical device. The data storage device 478 may be, for example, a non-volatile memory device, such as a PROM, EPROM, or Flash memory. In other embodiments the data storage device 478 may be an RFID (Radio Frequency Identification) tag, bar code, etc. Similarly, the reader 392 may be structured however necessary to read the data set 479, 579 from the data storage device 478, 578. For example, the reader 392 may be an RFID reader, a bar code reader, an infrared reader, or a set of instructions in the processor 330.

FIG. 4 is a block diagram of the medical device of FIG. 3 after an authorized accessory has been attached or coupled to it, while FIG. 5 is a block diagram of the medical device of FIG. 3 after another authorized accessory has been attached using a different attachment method than in FIG. 4. More particularly, in FIG. 4, the accessory 477 is directly attached or coupled, for example wirelessly coupled to the medical device 300, while in FIG. 5, the accessory 577 is coupled through a port 517 on the medical device 300. If the accessory 577 is connected through the port 517, the medical device 300 could use, for example, inductive coupling to transfer connection and authentication information from the accessory to the medical device. Other types of potential coupling at the port 517 may include optical coupling, infrared transmission, or a direct wired connection.

In some embodiments, the accessory 477 or 577 may be a non-invasive blood pressure hose, a non-invasive blood pressure cuff, an ECG cable, an ECG electrode, pulse oximetry sensor, a respiration sensor, a communication accessory for transferring patient data, a communication accessory for notification of an event, or a communication accessory for interaction with medical personnel, for instance. If the accessory 477 is a patient parameter collecting accessory, the parameter may include capnography, pulse oximetry, non-invasive blood pressure, ECG with three or more leads, invasive blood pressure, temperature, heart rate, respiration rate or CPR performance monitoring, for example.

An accessory detector, which may or may not be part of a reader 392 determines if an accessory 477 is attached to the medical device 300. After the accessory 477 is attached to the medical device 300, regardless of how the accessory is attached or coupled, the reader 392 reads the data set 479 stored in the data storage device 478 of the accessory 477. The processor 330 uses the data stored within the accessory data set 479 and read by the reader 392 to determine if a preset authentication criterion is confirmed. The medical device 300, or the processor 330 within, then uses this determination to control a level of functionality of the medical device. In some embodiments, instead of the processor 330, an other processor determines whether operation of the medical device 300 is to be according to the advanced functionality or the basic functionality In some embodiments, when the accessory 477 is coupled to the housing 301, the medical device 300 is capable of the defibrillating and the basic functionality 352. Further, in some embodiments, the medical device 300 is additionally capable of the advanced functionality only when the accessory 477 is coupled to the housing 301 and it is determined that the preset authentication criterion is confirmed. An alternative operation method is for the medical device 300 to not be enabled for advanced functionality 353 until an authorized accessory is attached to it.

When both the basic functionality 352 and the advanced functionality 353 are enabled on the medical device 300, oftentimes the functionalities differ by level of service. For example, the basic functionality 352 of the medical device 300 may be to report a first aspect of a parameter monitored through the accessory 477, such as an instantaneous value of the monitored parameter, and the advanced functionality 353 may be to report a second aspect of the monitored parameter, for example a trend of values of the monitored parameter. In another example, the first aspect may be an instantaneous value of an oxygen saturation reading, and the second aspect is one of carboxyhemoglobin and methemoglobin. In yet another example, the basic functionality may be to report on processing a 3-lead ECG, and the advanced functionality is to report on processing ECG based on more leads. In still a further example, the basic functionality 352 may be to report one of ventricular fibrillation and ventricular tachycardia, and the advanced functionality 353 is to report on a detected STEMI. In another example, the advanced functionality 353 is to provide a full set of data for ST plotting, but the basic functionality 352 is to provide less than the full set for ST plotting. In yet another example the basic functionality 352 is an AED mode while the advanced functionality 353 is a manual mode.

Other examples of advanced functionality 353 of the medical device 300 include an information display functionality, a synchronized cardioversion therapy, or a pacing therapy.

In some embodiments, to read the data set 479, 579 of the respective accessory 477, 577, the processor 330 of the medical device 300 causes a query to be transmitted to the accessory. Then, the data set 479, 579 is received responsive to the query. In other embodiments, the data set 479, 579 is received responsive to attaching the accessory 477, 577 to the housing 301. In other embodiments, the data set 479, 579 is received responsive to power-on of the medical device 300. In some embodiments the data set 479, 579 received from the accessory 477, 577 may be encrypted. In such a case a decryption algorithm is applied by the processor 330 to determine whether the received data set confirms the authentication or does not confirm the authentication.

FIGS. 6A, 6B, and 6C are block diagrams of the medical device 300 of FIG. 3 after various example unauthorized accessories have been attached. Unlike the examples described with reference to FIGS. 4 and 5, where an authorized accessory was attached to the medical device 300 and the medical device was therefore capable of all of defibrillation 351, basic functionality 352, and advanced functionality 353, in FIGS. 6A, 6B, and 6C, an unauthorized accessory 677A, 677B, or 677C, is attached to the medical device. In some embodiments of the invention, attaching an unauthorized accessory to the medical device 300 causes the medical device to disable the advanced functionality 353 of the medical device.

Recall from above that the medical device 300 may use various methods to read data from the accessory. The difference with reference to FIGS. 6A, 6B, and 6C is that a valid set of data is not received from the accessory. In the example illustrated in FIG. 6A, the accessory 677A includes an accessory data set 679A stored in a data storage device 678A, however the data stored in the accessory data set does not satisfy the preset criterion at the medical device 300 to indicate that the accessory 677A is an authorized device. In the example of FIG. 6B, there is no data stored in the data storage device 678B, and therefore does not satisfy the preset criterion, because there is no data with which to make the determination. Finally, in the example of FIG. 6C, there is not even a data storage device present in the accessory 677, thus it is impossible to read data from such an accessory, and therefore the preset criterion is also not satisfied.

Thus, in embodiments of the invention, if no data set is received from the accessory, such as the accessory 677B or 677C, the authentication is not confirmed, and the advanced functionality 353 of the medical device 300 is disabled or is not enabled. Also, as stated above, if a data set 679A is present in the accessory 677A, but the data within the data set does not indicate that the accessory is an authorized device, then the advanced functionality 353 of the medical device 300 is disabled, or is not enabled.

In addition to disabling the advanced functionality 353 of the medical device 300, the medical device may take additional action when an unauthorized accessory is attached. For example, if the authentication is not confirmed, the medical device 300 may output a warning, such as a warning to the user that the advanced functionality is disabled because an unauthorized accessory is being used. Other actions may include the medical device 300 sending a notification to a manufacturer of the medical device if the authentication is not confirmed. In other embodiments, if the authentication is not confirmed, the medical device 300 generates and stores an internal record.

In some embodiments, the advanced functionality 353 of the medical device 300 is enabled, or not disabled, for a limited time after it is determined that the preset authentication criterion is not confirmed. In other words, the advanced functionality 353 of the medical device may be enabled for a period of time, or for a number of operations or events before becoming disabled. Oftentimes when in this mode the medical device 300 will generate a warning to the user, as described above, to alert the user that the advanced functionality 353 will be disabled before or in conjunction with the advanced functionality actually being disabled. This affords the user an opportunity to secure an authorized accessory and attach it to the medical device 300 without losing the advanced functionality 353.

Embodiments of the invention are also directed to a control system for a medical device for use with an accessory capable of collecting a parameter of a patient. The medical device is capable of at least a basic functionality, an advanced functionality, and of defibrillating the patient. In such an embodiment, the control system may include, for example, with reference to FIG. 3, a reader 392 structured to read a data set from the accessory, and a processor 330 coupled to the reader 392 and structured to determine whether the data set from the accessory confirms or not a preset authentication criterion about the accessory. In some embodiments the function of the reader 392 is included within the processor 330. When the accessory is coupled to the housing, the medical device is capable of the defibrillating and the basic functionality. Further, the control system is structured to enable the advanced functionality of the medical device only when the accessory is coupled to the housing and it is determined that the preset authentication criterion is confirmed. As described above, the control system may include the reader 392 and processor 330, or the control system may include other components adapted to control the operation of the medical device. Some of such components are described with reference to FIG. 9 below.

FIG. 7 is a conceptual diagram for explaining an operation of according to embodiments. In a procedure 730, the medical device 300 determines whether the attached accessory is authorized or not authorized. If the accessory is an authorized device, the medical device 300 operates in the full mode 782, where defibrillation 351, basic functionality 352, and advanced functionality 353 are all possible. If instead the accessory is not authorized, then the medical device 300 operates in partial mode 781, where defibrillation 351 and basic functionality 352 are possible, but where advanced functionality 353 is not possible.

FIG. 8 is a detailed block diagram showing components of an external defibrillator 800 made according to embodiments, which may be an embodiment of the medical device 300 of FIG. 3. These components can be, for example, in external defibrillator 100 of FIG. 1. Plus, these components of FIG. 8 can be provided in a housing 801, which is also known as casing 801.

External defibrillator 800 is intended for use by a user 880, who would be the rescuer. Defibrillator 800 typically includes a defibrillation port 810, such as a socket in housing 801. Defibrillation port 810 includes nodes 814, 818. Defibrillation electrodes 804, 808, which can be similar to electrodes 104, 108, can be plugged in defibrillation port 810, so as to make electrical contact with nodes 814, 818, respectively. It is also possible that electrodes can be connected continuously to defibrillation port 810, etc. Either way, defibrillation port 810 can be used for guiding via electrodes to person 82 an electrical charge that has been stored in defibrillator 800, as will be seen later in this document.

If defibrillator 800 is actually a defibrillator-monitor, as was described with reference to FIG. 2, then it will typically also have an ECG port 819 in housing 801, for plugging in ECG leads 809. ECG leads 809 can help sense an ECG signal, e.g. a 12-lead signal, or from a different number of leads. Moreover, a defibrillator-monitor could have additional ports (not shown), such as to receive accessories, and an other component 825 for the above described additional features, such as patient signals.

Defibrillator 800 also includes a measurement circuit 820. Measurement circuit 820 receives physiological signals from ECG port 819, and also from other ports, if provided. These physiological signals are sensed, and information about them is rendered by circuit 820 as data, or other signals, etc.

If defibrillator 800 is actually an AED, it may lack ECG port 819. Measurement circuit 820 can obtain physiological signals through nodes 814, 818 instead, when defibrillation electrodes 804, 808 are attached to person 82. In these cases, a person's ECG signal can be sensed as a voltage difference between electrodes 804, 808. Plus, impedance between electrodes 804, 808 can be sensed for detecting, among other things, whether these electrodes 804, 808 have been inadvertently disconnected from the person.

Defibrillator 800 also includes a processor 830. Processor 830 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 830 can be considered to have a number of modules. One such module can be a detection module 832, which senses outputs of measurement circuit 820. Detection module 832 can include a VF detector. Thus, the person's sensed ECG can be used to determine whether the person is experiencing VF.

Another such module in processor 830 can be an advice module 834, which arrives at advice based on outputs of detection module 832. Advice module 834 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 800 may further issue prompts for it, and so on.

Processor 830 can include additional modules, such as module 836, for other functions. In addition, if other component 825 is indeed provided, it may be operated in part by processor 830, etc.

A reader 892 may be included within the processor 830 as a reader module 892, or may be a separate circuit or function. The reader 892 may be coupled to any or all of the defibrillation port 810, the ECG port 819, and any other port that receives an accessory. The reader 892 may read data from the accessory. Then, the processor 830 may use a module, for example the other module 836, to determine whether the accessory is an authorized accessory. The determination may be made based on the data read from the accessory by the reader 892 and applying the read data to one or more preset authentication criteria. After it is determined whether or not the accessory is an authorized one, the processor may control which of the functionalities of the defibrillator 800 to enable or disable.

Defibrillator 800 optionally further includes a memory 838, which can work together with processor 830. Memory 838 may be implemented in any number of ways. Such ways include, by way of example and not of limitation, nonvolatile memories (NVM), read-only memories (ROM), random access memories (RAM), any combination of these, and so on. Memory 838, if provided, can include programs for processor 830, and so on. The programs can be operational for the inherent needs of processor 830, and can also include protocols and ways that decisions can be made by advice module 834. In addition, memory 838 can store prompts for user 880, etc. Moreover, memory 838 can store patient data.

Defibrillator 800 may also include a power source 840. To enable portability of defibrillator 800, power source 840 typically includes a battery. Such a battery is typically implemented as a battery pack, which can be rechargeable or not. Sometimes, a combination is used, of rechargeable and non-rechargeable battery packs. Other embodiments of power source 840 can include AC power override, for where AC power will be available, and so on. In some embodiments, power source 840 is controlled by processor 830.

Defibrillator 800 additionally includes an energy storage module 850. Module 850 is where some electrical energy is stored, when preparing it for sudden discharge to administer a shock. Module 850 can be charged from power source 840 to the right amount of energy, as controlled by processor 830. In typical implementations, module 850 includes one or more capacitors 852, and so on.

Defibrillator 800 moreover includes a discharge circuit 855. Circuit 855 can be controlled to permit the energy stored in module 850 to be discharged to nodes 814, 818, and thus also to defibrillation electrodes 804, 808. Circuit 855 can include one or more switches 857. Those can be made in a number of ways, such as by an H-bridge, and so on.

Defibrillator 800 further includes a user interface 870 for user 880. User interface 870 can be made in any number of ways. For example, interface 870 may include a screen, to display what is detected and measured, provide visual feedback to the rescuer for their resuscitation attempts, and so on. Interface 870 may also include a speaker, to issue voice prompts, etc. Interface 870 may additionally include various controls, such as pushbuttons, keyboards, and so on. In addition, discharge circuit 855 can be controlled by processor 830, or directly by user 880 via user interface 870, and so on.

Defibrillator 800 can optionally include other components. For example, a communication module 890 may be provided for communicating with other machines. Such communication can be performed wirelessly, or via wire, or by infrared communication, and so on. This way, data can be communicated, such as patient data, incident information, therapy attempted, CPR performance, and so on.

FIG. 9 is a detailed flow diagram illustrating example methods according to embodiments of the invention. An example flow 900, which accords to embodiments of the invention, operates within or in conjunction with a medical device for use with an accessory capable of collecting a parameter of a patient and capable of at least a basic functionality, an advanced functionality, and of defibrillating the patient. In the flow 900, after the accessory is coupled to the medical device, a process 904 receives a data set from the coupled accessory. Then, a process 908 determines whether a data set received from the accessory confirms or not a preset authentication criterion about the coupled accessory.

If the process 908 determines that the preset authentication criterion about the coupled accessory is not confirmed, then a process 910 disables the advanced functionality and then a process 914 collects the patient parameter. Instead, if the process 908 determines that the preset authentication criterion about the coupled accessory is confirmed, then the patient parameter is collected in the process 914 without the advanced functionality ever having been disabled in the process 910.

Returning back to the beginning of the flow 900, some of the optional processes that may be present in the flow 900 are illustrated in dashed boxes. Before the data set is received from the coupled accessory in the process 904, the accessory may be queried in a process 902. Further, if the data set received from the accessory is encrypted, then the data set may be de-crypted in a process 906. Finally, between the process 910 that disables the advanced functionality and the process 914 that collects the patient parameter, an optional process 912 generates a warning, for example, to the user, that the advanced functionality has been disabled. In other embodiments, the warning generated in the process 912 may be sent as a notification to a manufacturer of the device, or may be stored as a record. Other method steps are also possible without deviating from the scope of the invention, such as the functions and operations of various components described above with reference to the above figures. For instance, other methods may optionally include detecting whether the accessory is attached or not attached to the housing.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. A medical device for an accessory capable of collecting a parameter of a patient, comprising:
   a housing configured to couple with a remote accessory configured to collect a parameter of a patient;
   an energy storage module disposed within the housing configured to store an electrical charge and configured to deliver the electrical charge to the patient for defibrillating the patient, the medical device further configured to have basic functionality and advanced functionality;
   a processor disposed in the housing and configured to determine whether a data set received from the remote accessory confirms preset authentication criterion about the remote accessory, wherein the data set corresponds to information stored in a memory of the remote accessory; and a memory coupled to and accessible by the processor, the memory configured to store authentication and readiness information and to authenticate the accessory.

2. The medical device of claim 1, in which the advanced functionality of the medial device is enabled in response to confirming the authentication information against the preset authorization criterion.

3. The medical device of claim 2, in which the advanced functionality of the medical device is enabled for a limited time.

4. The medical device of claim 1, wherein advanced functionality of the medical device is disabled in response to failing to confirm the authentication information against the preset authorization criterion.

5. The medical device of claim 4, wherein a warning is displayed on a display in response to the failing to confirm the authentication information.

6. The medical device of claim 1, wherein the received data set is encrypted when received at the medical device.

7. The medical device of claim 1, wherein the remote accessory comprises an electrode.

8. The medical device of claim 7, wherein the electrode comprises an electrocardiogram electrode.

9. The medical device of claim 7, wherein the electrode comprises an defibrillation electrode.

10. A method in a medical device for use an accessory capable of collecting a parameter of a patient, comprising:
receiving a data set from a remote accessory;
determining whether the data set confirms a preset authentication criterion about the remote accessory;
disabling at least one function of the medical device in response to not confirming the data set received against the preset authentication criterion; and
collecting at least one patient parameter while the at least one function is disabled.

11. The method of claim 10, wherein the receiving a data set from a remote accessory comprises communicatively coupling the remote accessory to the medical device through a wireless communication channel.

12. The method of claim 10, further comprising, by the medical device, coupling of the remote accessory to a processor of the medical device, wherein the remote accessory comprises a defibrillation electrode and a memory, wherein the data set corresponds to information stored in the memory.

13. The method of claim 10, wherein the at least one function is enabled prior to confirming the authentication data.

14. The method of claim 10, further comprising collecting at least one patient parameter after the at least one function is enabled.

15. A control system for a medical device for use with an accessory capable of collecting a parameter of a patient, comprising:
a reader coupled to a medical device and configured to read a data set from a remote accessory coupled to the medical device, wherein the medical device is configured to defibrillate a patient;
a processor coupled to the reader and configured to determine whether the data set from the remote accessory confirms a preset authentication criterion about the accessory,
wherein the processor is further configured to enable at least one function of the medical device in response to determining that the preset authentication criterion is confirmed and the remote accessory is authenticated.

16. The control system of claim 15, wherein the at least one function of the medical device is enabled for a limited time.

17. The control system of claim 15, wherein the at least one function of the medical device is disabled in response to failing to confirm the authentication information against the preset authorization criterion.

18. The control system of claim 15, further comprising a decryption module configured to decrypt the received data set, wherein the received data set is encrypted when received at the medical device.

19. The control system of claim 15, wherein the remote accessory comprises an electrode.

20. The control system of claim 15, wherein the reader comprises a radio-frequency identification reader configured to couple the remote accessory to the medical device through a wireless communication coupling.

* * * * *